United States Patent [19]

Van Gorp et al.

US005607840A

[11] Patent Number: 5,607,840
[45] Date of Patent: Mar. 4, 1997

[54] PROTEIN HYDROLYSATE DERIVED FROM MUCOSA TISSUE

[75] Inventors: Cornelius L. Van Gorp, Lebanon, Ohio; Frederick Vosburgh, Fort Wayne, Ind.; Robert L. Schubert, II, Monroe, Ohio

[73] Assignees: Celsus, Inc., Cincinnati, Ohio; Consolidated Nutrition, L.C., Omaha, Nebr.

[21] Appl. No.: 225,427

[22] Filed: Apr. 8, 1994

Related U.S. Application Data

[63] Continuation of Ser. No. 983,810, Nov. 30, 1992, abandoned.

[51] Int. Cl.$^6$ ............... C12P 21/06; A23L 1/305; A23J 3/30; A61K 38/01
[52] U.S. Cl. ............... 435/68.1; 426/56; 426/657; 426/801; 426/807; 424/520; 435/262; 435/101; 514/2; 514/56; 530/416
[58] Field of Search ............... 435/68.1, 262, 435/101; 426/656, 657, 56, 801, 807; 424/520; 514/2, 56; 530/416

[56] References Cited

U.S. PATENT DOCUMENTS

| | | | |
|---|---|---|---|
| 4,130,555 | 12/1978 | Ohtsuka et al. | 260/117 |
| 4,361,587 | 11/1982 | Brule et al. | 426/42 |
| 4,389,423 | 6/1983 | Madsen | 426/417 |
| 4,443,540 | 4/1984 | Chervan et al. | 435/69 |
| 4,572,839 | 2/1986 | Guitteny et al. | 426/646 |
| 5,053,234 | 10/1991 | Anderson et al. | 426/59 |
| 5,356,637 | 10/1994 | Loosen et al. | 426/7 |

FOREIGN PATENT DOCUMENTS

| | | |
|---|---|---|
| 0274939 | 7/1988 | European Pat. Off. . |
| 889648 | 2/1962 | United Kingdom . |
| 992201 | 5/1965 | United Kingdom . |

OTHER PUBLICATIONS

Journal of Dairy Science, vol. 75 Suppl. 1, p. 267 (1992).

*Primary Examiner*—David M. Naff
*Attorney, Agent, or Firm*—Baker & Daniels

[57] ABSTRACT

A protein hydrolyzate is produced from mucosa tissue of pigs, cattle or sheep by providing an aqueous mixture of the tissue, hydrolyzing the tissue with a proteolytic enzyme at a salt concentration of less than 0.1 molar to produce a digest solution containing a protein hydrolyzate and polyanions including heparin, adsorbing the polyanions on an anion exchange resin, recovering the anion exchange resin containing adsorbed polyanions to provide a digest solution containing less than 2.9 u/ml residual heparin and recovering the protein hydrolyzate from the digest solution by screening or dehydration. The protein hydrolyzate contains less than 15% ash, between 9.5 and 11.5% total Kjeldahl nitrogen and between 5.0 and 7.0% alpha amino nitrogen. The protein hydrolyzate may be used in nutritional formulations such as to promote weight gain in newly weaned livestock and in medical formulations such as peritoneal dialysis fluids and formulations for use in enteral and parenteral nutrition.

7 Claims, No Drawings

PROTEIN HYDROLYSATE DERIVED FROM MUCOSA TISSUE

This is a continuation of application Ser. No. 07/983,810, filed Nov. 30, 1992, now abandoned.

BACKGROUND OF THE INVENTION

The present invention relates to a protein hydrolysate derived from animal tissue having an endothelial or mucosal component (hereafter "mucosa"), a process for its preparation, and the use of such a protein hydrolysate.

Protein hydrolysate by definition consists of a mixture of amino acids and short chain peptides obtained by the hydrolysis of various animal and vegetable proteins. Protein hydrolysates (also known as "peptones") are used as sources of amino acids, seasoning agents and in nutrition, among other things.

For both economic and environmental reasons, productive use is now being made of an increasing percentage of the waste material generated as a result of the slaughter of animals, such as livestock. A major use of livestock waste or other by-products (livestock "offal") is in the production of the blood anti-coagulant heparin.

It has been estimated that over 90% of the heparin currently used as a blood anti-coagulant is obtained from porcine intestinal mucosa. An aqueous solution containing the mucosa from the livestock offal is chemically (acid or alkaline) or enzymatically hydrolyzed, and the heparin is extracted from the hydrolyzed mucosa by well-established techniques, such as selective sorption using an ion exchange resin. The solution containing the digested tissues includes high concentrations of salt. This high concentration of salts in the digest solution prevents constituents other than certain anionic and polyanionic materials (such as heparin) from sticking to the resin during the sorption of these materials. Although the cost of such resin can be high, an advantage of this process is that it requires only a minimal amount of resin, since only enough resin is required to selectively remove the desired anionic or polyanionic materials from the digest solution.

The mucosa and the digest solution also generally contain an additional salt component. This additional salt component is introduced into the solution in the form of an oxygen scavenger, bacteriostat or bacteriocide, typically sodium bisulfite, added to stabilize the raw material and to prevent bacterial growth.

The high residual concentration of salt in the digest solution renders the un-sorbed portion of the digest, which includes most of the proteins, largely useless for most practical purposes. These salt and sulfite levels not only make this protein sidestream inedible, but also potentially toxic for prolonged usage such as in agriculture as a source of nitrogen. The sidestream may also be toxic to those animals or humans allergic to sulfites.

The heparin-depleted digest solution is typically discarded or spread on farm land, since cost-effective ways have not been found to separate the organic components in the solution from the dissolved salt. The discarded solution, however, includes many high quality proteins in the form of protein hydrolysate. Rather than discarding these proteins, it is desirable to utilize them as a source of protein for human or animal nutrition. Additional use can be made of the proteins in microbial nutrition, such as vat fermentation.

Waste disposal costs of solutions of animal waste products continue to increase, and environmental regulations govern the manner in which high BOD materials, such as the heparin-depleted digest, may be disposed. The costs associated with disposal add not only to the cost of processing the livestock, but also to the cost of the heparin produced by this process.

Protein hydrolysates may be produced by either chemical or enzymatic methods. In acid hydrolysis, strong acids at elevated temperatures are used to break the glycosidic bond in the protein molecule. This relatively harsh treatment can result in damage to the heparin as well as some loss of essential amino acids. The treatment can also result in undesirable side reactions. Similarly, alkaline hydrolysis requires fairly extreme conditions for producing this reaction. Furthermore, the large amount of residual acid or alkali in the hydrolysate must be neutralized. This neutralization increases the salt content of the hydrolysate, and thereby further limits its potential use in nutritional formulations seeking minimum salt content.

Enzyme hydrolysis is an effective alternative to chemical treatment. This process is mild in comparison to acid or alkali hydrolysis. Additionally, the inherent specificity of several proteolytic enzymes can control the nature and extent of hydrolysis, and thus the functional properties of the end product. An important use of enzymatically hydrolyzed proteins is in human nutrition. Additionally, the proteins may be used in medical nutrition for undernourished persons, or those persons unable to properly digest and absorb whole protein. For example, it has been postulated that in cases of severe pancreatic insufficiency or malabsorption, that amino acids are better absorbed from hydrolyzed protein than from intact protein.

An initial source of pre-digested protein was milk, which has drawbacks such as poor palatability and high cost. Recently, individual crystalline amino acids have been formulated to mimic the amino acid profile of the protein hydrolysate obtained by hydrolysis of casein. Medical studies, however, have shown that di- and tripeptides such as can be produced by protein hydrolysis, are absorbed through the intestinal mucosa more effectively than the individual crystalline amino acids. Aside from the potential danger of allergic reactions to such crystalline amino acids, often produced by fermentation, such protein hydrolysate formulations are extremely expensive and out of reach for the world population at large.

Nutritional uses of the protein hydrolysate of the present invention include such specialty feeds as milk replacers for calf, piglet and other weaning mammals; protein extender for animal feed; and as an amino acid supplement, flavor or protein enhancer for human food and pet food. Research has shown that the high ash in peptone, or hydrolysate, obtained by traditional processes, significantly depresses appetite and weight gain at moderate inclusion rates. See, e.g. *Journal of Dairy science*, 75(1): 267; 1992, incorporated herein by reference. Medicine to which this invention may be applied includes total parenteral nutrition, peritoneal dialysis fluid as an alternative to glucose, and as a protein extender in enteral nutrition. Additional use may be found in microbial nutrition for vat fermentation.

British Patent 992,201 describes the conventional procedure for producing heparin described above. The procedure involves the addition of cross-linked copolymers with quaternary functional groups to a heparin-containing digest, using an alkali, alkali earth metal, or ammonium salt as a catalyst. At least 0.1 mole of a dissolved salt must be present. The recommended salt is sodium chloride. This patent focuses on the isolation of heparin and certain other anionic and polyanionic impurities from the remaining constituents in the digest. The isolation of protein hydrolysates, in a contaminated form in the digest, is not addressed in this patent. The examples in the patent teach a 0.5 molar salt concentration to accomplish the separation of the heparin, representing the midpoint in a claimed range of 0.1–1.0 molar.

After the anion exchange resin-heparin copolymer is harvested according to the procedure described in the British patent, the resulting protein-containing sidestream contains not only sodium chloride as a contaminant, but also the original sodium metabisulfite stabilizer, and the various biological materials (including protein hydrolysate) present in the raw materials that are not sorbed by the resin. These impurities left in the protein mother liquor after the harvesting of the resin-heparin copolymer render it largely useless for most practical applications.

Another commercial process presently in use for the production of heparin is based on the purification procedure described in British Patent 889,648. This process consists of treating a heparin-containing digest, which has previously been filtered to clarity, with 2 to 5% of salt and sufficient water soluble quaternary ammonium salt to selectively precipitate substantially all the heparin, but insufficient to precipitate other animal components. The protein sidestream of this process also contains a high percentage of salt. Furthermore, most quaternary ammonium salts are effective bacteriocides thus rendering any resulting protein unsuitable for fermentation. Process waste waters containing quaternary ammonium salts also have an adverse effect on municipal sewage operations.

A common thread of the two processes described above is that only limited use may be made of the heparin-depleted protein sidestream due to its high residual salt content. A need exists for a process for treating animal tissue, and particularly livestock offal, that minimizes the waste of that tissue and enables beneficial use to be made of the protein hydrolysate that may be derived from the tissue.

SUMMARY OF THE INVENTION

The aforementioned need is met by the present method for preparing a protein hydrolysate and by the protein hydrolysates prepared by the method. The protein hydrolysates of the present invention are derived from animal tissue having endothelial components. According to the present invention, a protein hydrolysate in virtually pure form may be produced by treating digested mucosa tissue with less than 0.5 molar salt, and preferably less than 0.1 molar the salt being an alkali metal salt, an alkali earth metal salt, an ammonium salt of an acid, or a mixture thereof.

A sufficient amount of anion-exchange resin is used in the present invention to enable the adsorption of virtually all of the polyanion "impurities" in the digest, with the protein hydrolysate remaining in the digest. These impurities, which include heparin, are present as glycosaminoglycans, nucleic acids or other such entities in the starting material. The protein hydrolysate, thus isolated, is void of these impurities. The protein hydrolysate is also void of the inherent disadvantages of the protein hydrolysate produced by conventional processes. A protein hydrolystate produced by the method of the present invention may have the following properties, on a dried basis: less than 15% ash; between 9.5 and 11.5% total Kjeldahl nitrogen; and between 5.0 and 7.0% α amino nitrogen. In addition, the hydrolysate may have an amino acid profile having the following properties on a dried basis: between 4.5 and 6.0% glycine; between 5.5 and 7.0% lysine; between 0.5 and 2.5% methionine; between 1.5 and 3.5% serine; between 4.5 and 7.0% leucine; and between 10.0 and 12.5% glutamic acid.

DETAILED DESCRIPTION OF THE INVENTION

The raw material for use in the inventive process for producing protein hydrolysates is animal tissue having an endothelial or mucosal component (mucosa). Typical raw materials envisioned for use in the process are livestock by-products, including gastrointestinal, tracheal or bronchial tissues, or other offal or non-offal tissues. The process water of livestock or meat processing establishments may also serve as a raw material.

When the raw material is transported or stored for a period of time before processing, it is preferably treated by physical or chemical means to inhibit bacterial growth. Physical means include temperature elevation into the range between 50 degrees C. and 95 degrees C. Chemical means include the use of a bacteriostat or bacteriocide. The purity of the protein hydrolysate may be optimized by using mucosa tissue which has been stabilized with a minimal amount of a bacteriostat such as an oxygen scavenger. Sodium metabisulfite is an example of an oxygen scavenger that has been found suitable. Another suitable preservative is calcium propionate, a preservative which is generally recognized as safe (GRAS) in food, and therefore is not subject to the restrictions associated with the use of bisulfites in food for humans. Other suitable preservatives that may be utilized in certain applications include bacteriostats such as BHT and BHA, and antibiotics that are known to be suitable for animal feed applications.

A preferred source of the mucosa raw material is government inspected pork intestines. Additional sources of suitable raw material include, for example, intestinal mucosa, intestinal skin or adventitia, trachea, lung and liver of animals such as pigs, cattle or sheep. Prior to digestion, the raw material may initially be subjected to ultrafiltration or reverse osmosis to reduce the water and salt content of the tissue. This removed "tissue water" includes a certain amount of salt; therefore its removal prior to digestion reduces the salt content in the final product.

If the raw material is to be transported or stored, a stabilizer, such as 0.5% (w/v) sodium metabisulfite or, preferably, 0.5% (w/v) calcium propionate, is added; or the raw material is maintained at an elevated temperature between 55° C. and 90° C.

The raw material is then introduced into a vat for processing. The raw material may be extracted under nonproteolytic conditions of certain molecules that are functionally destroyed by enzymes, such as proteoglycans which may have different properties than the glycosaminoglycans left after digestion. An extracting salt, such as guanidine hydrochloride, is added. The extracted constituents and extracting salts are separated from the tissues in a conventional manner, such as by centrifuge or filtration.

The resulting mucosa tissue is then heated to 55° C. Optionally, the tissue may first be heat denatured at 90° C. The pH is adjusted to an appropriate level for the enzyme with an appropriate agent, such as liquid caustic soda. The particular pH level may differ depending on the characteristics of the particular enzyme used. Approximately 1.5 gram of enzyme per kilo mucosa tissue is then added to hydrolyze the tissue. Under constant agitation, hydrolysis is continued for a time period between 4 and 24 hours, while maintaining the temperature at 45°–65° C. to yield the desired hydrolysate. Enzymatic action is then interrupted by raising the temperature to 90° C. for about 30 minutes. The liquor is screened, cooled to 55° C. and passed through a body which is supplied with approximately 75 grams of an anion-exchange resin per liter of digested mucosal tissue. The unadsorbed filtrate is stocked and concentrated and, if desired, dried.

Evaporator and spray drier combinations may be used to economically yield a dry product having appropriate functional characteristics from the hydrolyzed solution. For example, a double-effect evaporator using 500–600 BTU to remove a pound of water may be used to concentrate the product to approximately 25% solids. A spray-drier requiring 1600–1800 BTU per pound of water may be used to arrive at a product of greater than 95% solids.

In a preferred embodiment, the solution is depleted of the impurities, including heparin and certain other anionic and polyanionic impurities, by selective sorption onto an anion exchange resin. Alternatively, other conventional separation techniques such as filtration or precipitation may be utilized to separate the "impurities" from the digest solution containing the protein hydrolysate.

The sorption of the impurities onto the resin takes place in the presence of reduced initial concentrations of salt when compared to the prior art methods. In the typical case, the concentrations of salt ranges from about 0.1–450 millimolar (0.0001–0.45 molar). The sorptive material may be an ion-exchanger, or an affinity resin. The prior art method for preparation of heparin utilizes a higher concentration of salt in the digest solution, in order to minimize the sorption of anions other than heparin. The present method, on the other hand, utilizes a lower salt concentration in order to increase the sorption of other anionic and polyanionic "impurity" materials in addition to heparin, thereby removing these materials from the digest containing the protein hydrolysate. If desired, the sorbed constituents may be selectively desorbed from the resin utilizing techniques known in the art, such as elution at increasing salt concentrations.

The material not sorbed initially will be primarily protein hydrolysate and various non-polar or non-anionic constituents under the solution conditions. The heparin-depleted solution, or a mixture with various fractions subsequently eluted from the ion-exchanger, may be utilized directly, or commingled with other materials before or after concentration, drying or further processing.

A larger amount of sorptive resin is utilized in the present method than in the prior art methods. The sorption of heparin and other impurities in the prior art method occurs at a sufficiently high salt concentration in the digest solution that the sorption of materials other than heparin is minimized. The larger amount of resin in the inventive method is required in order to assure the presence of a sufficient amount of resin to sorb the greater amount of anionic and polyanionic materials that adhere to the resin at the lower salt concentrations used in the inventive method. The sorption of the anionic and polyanionic materials can further be enhanced by either adjusting the pH of the digest to conditions conducive for adsorption to the resin, or by utilizing other chromatography techniques, such as radial flow.

The particular enzyme to-be utilized in the hydrolysis is selected from among those proteolytic enzymes that are typically considered to be of a foodgrade quality. Examples of enzymes that are acceptable are proteolytic enzymes of the Subtilisin family. These enzymes are isolated from the bacterium *Bacillus subtilis*, and are well known to those skilled in the art. Of this class, a foodgrade quality enzyme, such as Alcalase 2.4 L is preferred, although other grades or other enzymes are acceptable. Alcalase 2.4 L is commercially available from Novo-Nordisk of Bagsvaerd, Denmark.

Basic anion-exchange resins may be used in this invention for purification of the protein hydrolysate and for the isolation of anionic constituents. Such basic anion-exchange resins are commercially available, among others, under the trademarks Lewatit or Amerlite. An affinity resin, such as one containing anti-heparin, may also be used.

It is found that the protein hydrolysate obtained by the method of the present invention is low in ash, high in nitrogen and alpha amino nitrogen content, and particularly rich in glycine content.

For reference, the typical properties of the subject protein hydrolysate obtained by the method of the present invention are compared to those of other protein hydrolysates as shown below:

|  | Casein | Lactalbumin | Plasma | Soy | Mucosa |
|---|---|---|---|---|---|
| Total Nitrogen %, d.b. | 13.3 | 12.3 | 10.9 | 9.5 | 9.8 |
| Ash %, d.b. | 8.2 | 4.0 | 15.0 | 11.5 | 13.8 |
| Sodium %, d.b. | 3.3 | 0.9 | 6.25 | 2.7 | 4.6 |
| Chloride %, d.b. | 1.1 | 0.56 | N.A. | 2.7 | 2.4 |
| Amino Acid as % of Total Protein |  |  |  |  |  |
| Alanine | 3.7 | 4.6 | 4.4 | 3.8 | 7.1 |
| Arginine | 4.6 | 2.7 | 6.9 | 8.4 | 2.4 |
| Aspartic Acid | 6.7 | 10.1 | 9.2 | 12.8 | 6.9 |
| Cystine | 0.4 | 2.6 | 3.2 | 1.0 | 1.0 |
| Glutamic Acid | 18.9 | 19.9 | 12.9 | 21.1 | 16.2 |
| Glycine | 2.0 | 2.1 | 3.5 | 4.0 | 7.6 |
| Histidine | 1.9 | 1.6 | 3.6 | 2.3 | 2.5 |
| Hydroxyproline | — | — | — | — | — |
| Isoleucine | 5.9 | 5.2 | 2.8 | 4.3 | 5.1 |
| Leucine | 9.2 | 11.3 | 8.0 | 7.1 | 9.4 |
| Lysine | 8.4 | 9.2 | 8.8 | 6.1 | 9.0 |
| Methionine | 2.4 | 2.6 | 0.8 | 1.8 | 2.9 |
| Phenylalanine | 5.2 | 3.7 | 5.4 | 4.3 | 4.9 |
| Proline | 9.2 | 4.7 | 5.9 | 5.3 | 6.2 |
| Serine | 5.2 | 4.5 | 5.6 | 5.2 | 2.7 |
| Threonine | 5.0 | 4.5 | 6.0 | 4.2 | 5.5 |
| Tryptophan | 1.3 | 1.7 | 1.9 | 1.0 | 1.4 |
| Tyrosine | 3.0 | 2.7 | 5.1 | 3.0 | 2.8 |
| Valine | 7.0 | 6.3 | 6.0 | 4.3 | 6.4 |
|  | 100.0 | 100.0 | 100.0 | 100.0 | 100.0 |

This invention will be further illustrated by the following examples. The examples are only provided as illustrations, and are not intended to be limiting in any manner of the scope of this invention.

EXAMPLE 1

Mucosa tissue, stabilized with approximately 25 grams of sodium metabisulfite per liter of tissue, was digested with a proteolytic enzyme of the Subtilisin family at pH 8.6 under mild heat, resulting in 1825 ml digested material having a heparin activity of 60 u/ml. 3 grams of sodium chloride per liter and 120 ml of an anion exchange resin per liter of mucosa tissue were added to the digest, and reacted for 23 hours under continuous agitation. The resin was then harvested. The filtrate had a residual heparin activity of <2.9 u/ml reflecting a 95% extraction yield, which is considered satisfactory. The filtrate had the following properties:

| | | |
|---|---|---|
| Oil & Grease | 5200 mg/l <EPA 413.1> | |
| Total BOD (5 day) | 124,000 mg/l <SM 5210> | |
| Total Suspended Solids | 24,600 mg/l <EPA 160.2> | | and had an amino acid profile as follows:

| | mM Conc. (free) | Mm Conc. (total) |
|---|---|---|
| Aspartic Acid | 58.7 | 109.2 |
| Threonine | 55.9 | 62.9 |
| Serine | 61.7 | 23.9 |
| Glutamic Acid | 95.0 | 151.6 |
| Proline | 51.5 | 66.8 |
| Glycine | 79.8 | 141.5 |
| Alanine | 103.8 | 111.7 |
| Cystine | — | — |
| Valine | 83.3 | 82.1 |
| Methionine | 21.3 | 19.0 |
| Isoleucine | 51.5 | 53.3 |
| Leucine | 104.2 | 108.5 |
| Tyrosine | 3.0 | 18.3 |
| Phenylalanine | 34.2 | 37.1 |
| Histidine | 36.6 | 42.5 |
| Tryptophan | — | — |
| Lysine | 77.8 | 101.3 |
| Arginine | 54.1 | 66.5 |
| Ammonia | 71.5 | 167.1 |

EXAMPLE 2

2125 ml of porcine mucosa tissue stabilized with 0.5% (w/v) sodium metabisulfite was digested with a proteolytic enzyme of the Subtilisin family at pH 8.4 under mild heat resulting in 2000 ml digested material with a heparin activity of 58 u/ml.

The digest was split into two equal parts:

(1) 1000 ml was processed in the same manner as Example 1 except that the amount of sodium chloride was increased to 5 grams per liter. The resin was slurried for only 18 hours. The heparin potency of the filtrate, after the isolation of resin, was 2.8 u/ml.

(2) 1000 ml was processed in an identical manner as Example 1 except that no sodium chloride was added and the resin contact was increased to 24 hours. After isolation of the resin, the heparin activity of the filtrate was assayed at 2.8 u/ml.

EXAMPLE 3

Mucosa tissue was collected and stabilized with 0.5% (w/v) calcium propionate. The pH was adjusted to 8.3 with 50% caustic soda, 1 gram of enzyme was added per liter of mucosa tissue and the slurry was held at 55° C. for 60 hours. Typical odor was observed but no spoilage had occurred. Enzyme action was stopped by heating to 90° C., holding for 15 minutes, and subsequently cooling to 55° C. 150 ml of resin per liter of slurry was added to adsorb all polyanions. After the resin-polyanion copolymer was harvested, the filtrate was analyzed. The heparin activity of the filtrate was assayed at <7 u/ml.

| | |
|---|---|
| Solids, % | 21.7 |
| Ash, % | 2.99 |
| Kjeldahl Nitrogen, % | 2.11 |
| Total Phosphorous, % | 0.27 |
| Sodium, % | 0.99 |
| Chloride, % | 0.51 |
| Sulfite, ppm | 8.2 |

-continued

| Amino Acid Analysis | % Total | % Free |
|---|---|---|
| Aspartic Acid | 0.80 | 0.40 |
| Threonine | 0.63 | 0.45 |
| Serine | 0.31 | — |
| Glutamic Acid | 1.87 | 1.23 |
| Proline | 0.71 | 0.56 |
| Glycine | 0.87 | 0.50 |
| Alanine | 0.82 | 0.69 |
| Cystine | 0.11 | — |
| Valine | 0.74 | 0.62 |
| Methionine | 0.33 | 0.22 |
| Isoleucine | 0.59 | 0.49 |
| Leucine | 1.08 | 0.89 |
| Tyrosine | 0.32 | 0.26 |
| Phenylalanine | 0.56 | 0.45 |
| Histidine | 0.29 | 0.25 |
| Lysine | 1.04 | 0.82 |
| Arginine | 0.28 | 0.08 |
| Tryptophan | 0.16 | — |
| | 11.51 | 7.91 |

EXAMPLE 4

Protein hydrolysate prepared according to Example 1 was fed under controlled conditions to newly weaned piglets. It is well known that maximum weight gain in newly weaned livestock is critical to their subsequent health and efficient growth. For this reason, proteins or other feed ingredients that enhance this early growth are of significant value.

Currently, the inclusion of spray dried animal blood plasma in diets for young pigs induces the greatest observed weight gain, and therefore sells for approximately 20 times the cost of average swine feeds. However, the supply of plasma is limited, with twice as much fed per baby pig as is recovered from a pig at slaughter. With this intrinsic imbalance between supply and demand, the price involved with the use of plasma can be expected to continue to increase even from the current level.

As an alternative to plasma, a hydrolysate (i.e., a peptone) produced from the mucosa of livestock by the inventive process was fed to newly weaned, commercial hybrid piglets. In piglet feeding experiments, hydrolysate, containing less than 15% (low ash) or approximately 30% (traditional) ash was fed as 5% of the diet in side-by-side trials against identical diets, except with plasma substituted for the hydrolysate as a bench mark for maximum performance. The results are shown in Table 1.

TABLE 1

| PIGLET FEEDING TRIAL[1] | | |
|---|---|---|
| Hydrolysate | Appetite[2] | Weight Gain[3] |
| low ash[4] | 107% | 111% |
| Traditional[5] | 84% | 83% |

Notes:
[1]Results are normalized against plasma performance and reported in percent.
[2]Appetite was measured as feed consumed by pigs of equal weight, age and genetic composition.
[3]Weight gain was measured as the difference in weight over the length of the trial.
[4]Differences between plasma and low ash peptone effects are not statistically significant (p < .05).
[5]Statistically significant depression in appetite and weight gain (p < .05) occurs with traditional peptone.

Protein hydrolysate is equally as effective as plasma, but at a significantly lower production cost. Furthermore, protein hydrolysate is an economic alternative to plasma. The cost of the raw mucosa is lower than raw plasma; it is less expensive to process; and income from the sale of the crude heparin that can be isolated from its sidestream in the inventive process generates added revenue without decreasing the value of the hydrolysate. Hydrolysate produced from mucosa in the traditional heparin isolation process has substantial added salt that contributes to an unalterably high ash content that significantly detracts from its value as a feed ingredient. The inventive process therefore enables productive use to be made of not only the heparin, but also the previously discarded hydrolysate.

While this invention has been described as having a preferred embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method for the preparation of protein hydrolysate for use in providing nutrition from mammalian mucosa tissue, comprising the steps of:

providing an aqueous mixture comprising said mammalian mucosa tissue, said mammalian mucosa tissue being essentially the only tissue present in the aqueous mixture, said mucosa tissue being at least one of intestines, intestinal mucosa, intestinal skin, trachea tissue, lung tissue and liver tissue, and being derived from at least one of pigs, cattle and sheep;

hydrolyzing the mucosa tissue in said aqueous mixture with a proteolytic enzyme at a salt concentration of less than 0.1 molar, said salt being an alkali metal salt, an alkali earth metal salt, an ammonium salt of an acid, or a mixture thereof, said hydrolysis being performed at a pH of about 8.5 and at a temperature between about 45° C. and about 65° C., thereby forming a digest solution comprising said protein hydrolysate and polyanions, said polyanions comprising heparin, said salt concentration being conducive for separation of said polyanions comprising heparin from said protein hydrolysate by adsorption of said polyanions comprising heparin with an anion exchange resin;

adding a sufficient amount of said anion exchange resin to said digest solution to adsorb said polyanions comprising heparin from said digest solution onto said anion exchange resin;

recovering said anion exchange resin and said adsorbed polyanions comprising heparin from said digest solution, a sufficient amount of said polyanions comprising heparin being adsorbed onto said resin and removed from said digest solution such that said digest solution has a residual heparin activity of less than about 2.9 u/ml; and recovering the protein hydrolysate from the digest solution by at least one of screening and dehydration, said protein hydrolysate having the following properties on a dried basis: (a) less than 15% ash (b) between 9.5 and 11.5% total Kieldhal nitrogen, and (c) between 5.0 and 7.0% alpha amino nitrogen.

2. The method of claim 1 wherein said aqueous mixture is hydrolyzed at a temperature of about 55° C.

3. The method of claim 1, wherein the mucosa tissue is derived from intestines.

4. The method of claim 1, wherein said protein hydrolystate is recovered from the digest solution by drying the digest solution.

5. The method of claim 1, wherein said polyanions comprising heparin are recovered from the anion exchange resin by selective elution at increasing salt concentrations.

6. A protein hydrolysate prepared by the method of claim 1.

7. The protein hydrolystate of claim 6, wherein said protein hydrolysate has the following percentages of amino acids based on percent dry basis

| Glycine | 4.5–6.0% |
| Lysine | 5.5–7.0% |
| Methionine | 0.5–2.5% |
| Serine | 1.5–3.5% |
| Leucine | 4.5–7.0%, and |
| Glutamic acid | 10.0–12.5%. |

* * * * *

UNITED STATES PATENT AND TRADEMARK OFFICE
CERTIFICATE OF CORRECTION

PATENT NO. : 5,607,840
DATED : March 4, 1997
INVENTOR(S) : Cornelius L. Van Gorp et al.

It is certified that error appears in the above-indentified patent and that said Letters Patent is hereby corrected as shown below:

On the Title Page, Section [57], last line of Abstract, following "parenteral", delete "mutrition" and insert -- nutrition --.

Claim 1, column 10, line 18, after "total", delete "Kieldhal" and insert -- Kjeldahl --.

Claim 4, column 10, beginning on line 24 and continuing on line 25, after "protein", delete "hydrolystate" and insert -- hydrolysate --.

Claim 7, column 10, line 32, after "protein", delete "hydrolystate" and insert -- hydrolysate --.

Signed and Sealed this

Fifth Day of August, 1997

*Attest:*

BRUCE LEHMAN

*Attesting Officer*    *Commissioner of Patents and Trademarks*